(12) United States Patent
Michalski

(10) Patent No.: US 11,160,934 B2
(45) Date of Patent: Nov. 2, 2021

(54) CONICAL NEEDLE AND METHODS OF USE AND MANUFACTURING

(71) Applicant: Nestlé Skin Health SA, Lausanne (CH)

(72) Inventor: Marcin Michalski, Neurnberg (DE)

(73) Assignee: GALDERMA HOLDING SA

( * ) Notice: Subject to any disclaimer, the term of this patent is extended or adjusted under 35 U.S.C. 154(b) by 0 days.

(21) Appl. No.: 16/611,300

(22) PCT Filed: May 9, 2018

(86) PCT No.: PCT/IB2018/053234
§ 371 (c)(1),
(2) Date: Nov. 6, 2019

(87) PCT Pub. No.: WO2018/207119
PCT Pub. Date: Nov. 15, 2018

(65) Prior Publication Data
US 2020/0164158 A1  May 28, 2020

Related U.S. Application Data

(60) Provisional application No. 62/504,151, filed on May 10, 2017.

(51) Int. Cl.
*A61M 5/32* (2006.01)
*B21G 1/00* (2006.01)

(52) U.S. Cl.
CPC ............. *A61M 5/3286* (2013.01); *B21G 1/00* (2013.01); *A61M 2207/00* (2013.01)

(58) Field of Classification Search
CPC .................... A61M 5/3286; A61M 2207/00
See application file for complete search history.

(56) References Cited

U.S. PATENT DOCUMENTS 4,838,877 A * 6/1989 Massau ............... A61M 5/3286
604/264
2010/0137804 A1* 6/2010 Wiley ............... A61M 25/0067
604/168.01
(Continued)

FOREIGN PATENT DOCUMENTS

DE  202 11 110 U1  9/2002
DE  102 48 377 A1  5/2004
(Continued)

*Primary Examiner* — Nathan R Price
*Assistant Examiner* — John A Doubrava
(74) *Attorney, Agent, or Firm* — Ice Miller LLP

(57) ABSTRACT

A conical needle includes a hollow needle body has a distal end and a proximal end. The needle body has a substantially consistent cross-sectional diameter along the entire length of a central longitudinal axis of the needle body between the proximal end and the distal end of the needle body. The interior of the needle body defines a fluid pathway extending along the longitudinal axis. A conical portion is located at the distal end of the needle body. The conical portion has a sidewall, a distal end, and a proximal end. The conical portion forms a sharp tip located at the distal end of the conical portion. A lateral opening is located fully within the sidewall of the conical portion. The lateral opening is in fluid communication with the fluid pathway.

19 Claims, 4 Drawing Sheets

(56) References Cited

U.S. PATENT DOCUMENTS

2012/0083749 A1* 4/2012 Kawamoto ...... A61B 5/150282
                                                                604/239
2016/0338734 A1* 11/2016 Shah ................ A61B 5/14503
2017/0119974 A1* 5/2017 Racz ................. A61B 17/3401

FOREIGN PATENT DOCUMENTS

WO    2007/121143 A2    10/2007
WO    2010/026644 A1    3/2010

\* cited by examiner

CONICAL NEEDLE AND METHODS OF USE AND MANUFACTURING

CROSS REFERENCE TO RELATED APPLICATIONS

This application is a Section 371 of International Application No. PCT/IB318/053234, filed May 9, 2018, which was published in the English language on Nov. 15, 2018, under International Publication No. WO 2018/207119, and also claims priority to U.S. Patent Application No. 62/504,151, filed May 10, 2017 and entitled "Conical Needle and Methods of Use", the entire contents of which are incorporated herein by reference in their entirety.

FIELD OF THE INVENTION

The present invention relates to a conical needle for an injection device for delivering liquid or gel compositions. It also relates to methods of administration of a liquid or gel composition using the conical needle.

BACKGROUND OF THE INVENTION

The problem of bruises as a result of medical injections is due to the damage of the blood vessels present in the skin and other tissues. Damage of blood vessels occurs, when they are cut by the sharp edge of a beveled needle penetrating the tissue (See FIGS. 1A-1C). To add to the complexity, and even though it is observed that some patients and some parts of the body are more prone to developing bruises than others, there is a high degree of randomness involved in the process, since there is no way of avoiding all vessels and even very small vessels can cause bruises if they are damaged.

Previous efforts to minimize bruises include blunt-end cannulas in which a small incision is made using a sharp needle followed by the injection of the substance itself being performed using a cannula thus generating a much smaller risk of damaging a blood vessel. This method is partially successful but cumbersome as a procedure and it still requires a sharp needle to penetrate the tissue initially. Therefore, there is a need for new devices and methods which reduce or eliminate the risk of bruises generated in injection procedures. It is desirable to design, develop, construct and develop a device and method for minimizing bruises when conducting medical injections and the preferred invention herein addresses the shortcomings of known prior art devices.

BRIEF SUMMARY OF THE INVENTION

Briefly stated, the preferred invention is directed to a conical needle including a hollow needle body having a distal end and a proximal end. The needle body has a substantially consistent cross-sectional diameter along the entire length of a central longitudinal axis of the needle body between the proximal end and the distal end of the needle body. The interior of the needle body defines a fluid pathway extending along the longitudinal axis. A conical portion is located at the distal end of the needle body. The conical portion has a sidewall, a distal end, and a proximal end. The conical portion forms a sharp tip located at the distal end of the conical portion. A lateral opening is located fully within the sidewall of the conical portion. The lateral opening is in fluid communication with the fluid pathway.

In another aspect, the preferred invention is directed to a method for percutaneous administration of a liquid or gel composition into a patient. The method includes the steps of penetrating an epidermis of the skin of the patient at a desirable skin region by pressing a conical needle with a sharp tip at a distal end of a conical portion of the conical needle against the skin to create an opening in an epidermis of the patient and administering the liquid or gel composition through a lateral opening in the conical portion of the needle. The lateral opening is positioned entirely within the conical portion and the liquid or gel composition is injected laterally away from a longitudinal axis of the conical needle.

In another aspect, the preferred invention is directed to a method for manufacturing a conical needle. The method includes the steps of bending or turning a blunt-tipped, hollow needle and grinding a tip portion of the blunt-tipped, hollow needle to form a conical portion having a sharp tip at a distal end of the conical portion and a lateral opening located fully within a sidewall of the conical portion.

BRIEF DESCRIPTION OF THE SEVERAL VIEWS OF THE DRAWINGS

The details of one or more embodiments of the subject matter described in this specification are set forth in the accompanying drawings and the description below. Other features, aspects and advantages of the subject matter will become apparent from the description, the drawings and the claims. For the purposes of illustrating the conical needle and related methods, there is shown in the drawings preferred embodiments of the conical needle. It should be understood, however, that the application is not limited to the precise arrangements and instrumentalities shown. In the drawings:

DETAILED DESCRIPTION OF THE INVENTION

Figure 1A:
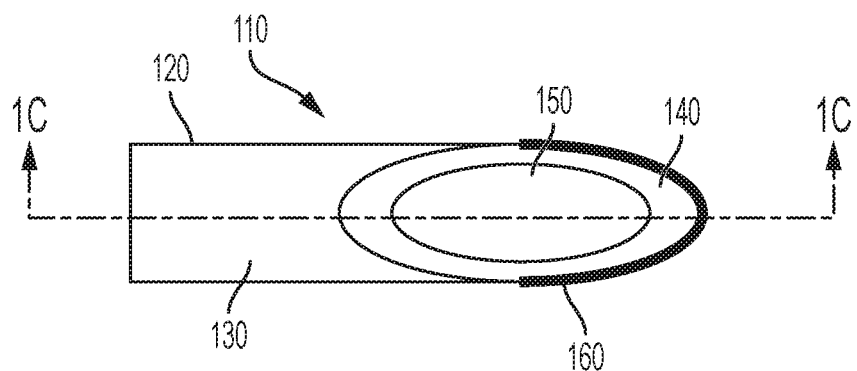
FIG. 1A is a top plan view of a prior art beveled hypodermic needle with a sharp cutting edge.

For clarity herein, it is understood that the word "distal" refers to a direction closer relative to an injection device, while the word "proximal" refers to a direction relatively further from the injection device. For example, the end of a needle placed within the body of a patient is considered a proximal end of the needle, while the needle end remaining outside the body and in communication with the syringe is a distal end of the needle.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred hypodermic needle and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 1B:
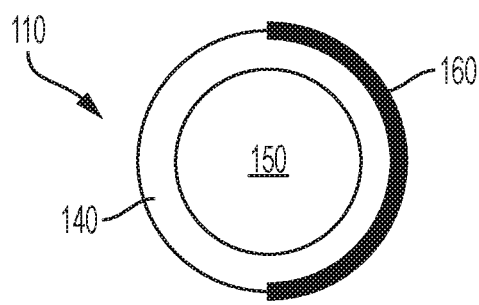
FIG. 1B is a front elevational view of the prior art hypodermic needle of FIG. 1A.
Figure 1C:
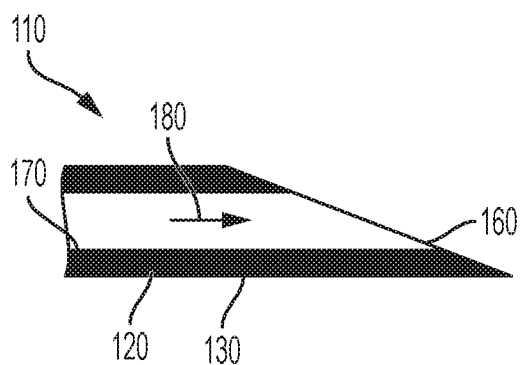
FIG. 1C is a cross-sectional view of the prior art hypodermic needle of FIG. 1A, taken along line 1C-1C of FIG. 1A.

Referring to FIGS. 1A-1C, needles for injecting fluid into a patient are generally known in the medical arts as being formed from a generally cylindrical tube defining a hollow needle body having a central longitudinal axis, a proximal end and a distal end adapted for penetration into the body cavity of a subject, and a fluid pathway extending completely through the needle body. Such a prior art needle, which is comprised of a standard bevel needle 110, is shown in FIGS. 1A-1C. As discussed in the Background of the Invention section, there exists in the prior art the standard beveled needle 110 that includes a beveled face 140 at the distal end with a sharp cutting surface or edge 160 for insertion into the patient for injection. The beveled face 140 includes an opening 150 at the distal end in fluid communication with a fluid pathway 180. Damage of blood vessels occurs when the blood vessels are cut by the sharp edge 160 of the standard prior art beveled needle 110 penetrating the tissue, which leads to bruising in the patient.

Referring to FIGS. 1A-4, it is an object of the first preferred invention to reduce or eliminate the above-mentioned and other drawbacks of the standard beveled needle 110 and related needles with sharp penetrating edges, such as the sharp beveled edge 160, that have a tendency to cut and damage blood vessels during injection. This object is achieved by a conical needle design as defined in the preferred hypodermic needle, generally designated 210, described herein.

In accordance with a first preferred embodiment of the present invention, there is provided the first preferred conical hypodermic needle 210, which is preferably comprised of a conical needle. The preferred needle 210 is comprised of a conical needle with a substantially conical distal end or conical portion 270. The preferred distal conical portion 270 of the conical needle 210 replaces the sharp cutting edge 160 of the standard prior art beveled needle 110 with a sharp tip 250 and an injection opening 240 is moved to the side of the preferred needle 210. The sharp tip 250 is preferably positioned on a longitudinal axis 225 of the conical needle 210 and the injection or lateral opening 240 is preferably spaced from and directed laterally away from the longitudinal axis 225. The fluid pathway 282 is also preferably positioned coaxially on the longitudinal axis 225 in the needle body 220 and extends away from the longitudinal axis, at least partially, in the conical portion 270. Such a design of the preferred needle 210 improves upon the prior art by preventing the blood vessels from being cut, hence reducing bruising. The conical needle 210 reduces the damage to the blood vessels, because the blood vessels are pushed to the side instead of being cut during tissue penetration, which often happens with the sharp beveled edge 160.

In accordance with the first preferred embodiment of the present invention the conical needle 210 comprises a generally cylindrical tube or needle body 220 having a distal end 224 and a proximal end 222. A sharp tip 250 is located at a distal end 276 of the conical portion 270 and the conical portion 270 is attached to the distal end 224 of the needle body 220. The needle body 220 comprises an exterior surface 230 and an interior surface 280 defining a fluid pathway 282 that extends from the proximal end 222 of needle body 220 toward the sharp tip 250.

In accordance with the first preferred embodiment of the conical needle 210, the needle body 220 is integrally formed with the conical portion 210, which has the sharp tip 250 at the distal end 276. The lateral or injection opening 240 is positioned on the conical portion 270 between the sharp tip 250 and a transition between the distal end 224 of the needle body 220 and the proximal end 274 of the conical portion 270. The lateral opening 240 is preferably ovular in shape. The lateral opening 240 has an opening length L and an opening width W, wherein the opening length L is greater than the opening width W. A liquid or gel composition, nearly any variety of injectable medication or injectable material can be delivered through the fluid pathway 282, out of the injection opening 240 and into the patient. The conical needle 210 may be constructed of polished surgical steel and the lateral opening 240 may have a smooth design in order to avoid damage to the tissue while allowing the liquid or gel composition or other injectable material to flow easily through and out of the conical needle 210.

In accordance with the first preferred embodiment, the conical needle 210 is constructed of a needle having a twenty-seven to twenty-nine gauge (2729 G) on the Birmingham Gauge scale, but is not so limited. The conical needle 210 may be comprised of a seven to thirty-four gauge (7-34 G) needle or more. The preferred conical needle 210, therefore, preferably has an outer wall diameter $D_O$ of approximately thirty-three hundredths millimeters (0.33 mm) to approximately forty-one hundredths millimeters (0.41 mm), an inner wall diameter $D_I$ of approximately eighteen hundredths millimeters (0.18 mm) to approximately twenty-one hundredths millimeters (0.21 mm), and a wall thickness T of approximately seventy-five thousandths millimeters (0.075 mm) to approximately ten hundredths millimeters (0.10 mm). Accordingly, the opening width W of the preferred conical needle 210 is defined by the inner wall diameter, preferably being within the range of approximately eighteen hundredths millimeters (0.18 mm) to approximately twenty-one hundredths millimeters (0.21 mm). The opening length L of the first preferred conical needle 210 is approximately twice the opening width W, therefore preferably being within the range of approximately thirty-six hundredths millimeters (0.36 mm) to approximately forty-two hundredths millimeters (0.42 mm). The conical needle 210 may also be of any other suitable gauge sufficient to provide for the injection opening 240 to be large enough to adequately dispense the desired liquid or gel composition or other injectable material, to withstand the normal operating conditions of the conical needle 210 and to perform the preferred functions of the conical needle 210, as is described herein.

In accordance with the first preferred embodiment of the conical needle 210, an injection apparatus may be provided, such as a traditional syringe or suitable alternative, wherein the proximal end 222 of the needle body 220 of the conical needle 210 is configured to attach to the syringe or other injection apparatus. More preferably, the proximal end 222 of the needle body 220 of the conical needle 210 is further configured to place the fluid pathway 282 in fluid communication with the syringe or other injection apparatus in order to form an injection device. For example, the proximal end 222 may include a Luer connector for attachment to a syringe.

In accordance with the first preferred embodiment of the conical needle 210, the use of the injection device for avoiding bruising during percutaneous injection of a liquid or gel composition or other injectable material or composition is described. The liquid or gel composition may be a liquid or gel composition for cosmetic treatment, where bruising from cutting of blood vessels is particularly undesirable.

In accordance with the first preferred embodiment of the invention, a method for percutaneous administration of a liquid or gel composition or other injectable materials is disclosed. The method preferably comprises the following preferred steps of: penetrating the epidermis at a desirable skin region by pressing the conical needle 210 with the sharp tip 250 at the distal end 276 against the skin to create an opening in the epidermis; and administering the liquid or gel composition or other injectable material through the lateral or injection opening 250 that is positioned in the conical portion 270 of the conical needle 210. The liquid or gel composition may include any medicament in liquid or gel form appropriate for injection into a patient. The liquid or gel composition may be administered at any level below the epidermis ranging from very superficially in the skin to being deposited on the bone. The liquid or gel composition may be administered at any level ranging from the superficial dermis to the periosteum. The liquid or gel composition or nearly any injectable material may be directed in a particular direction, such as toward the patient's skin or away from the patient's skin by directing the lateral or injection opening 240 toward or away from the skin, respectively.

In accordance with the first preferred embodiment of the method for percutaneous administration of a gel or liquid composition, the liquid or gel composition is for cosmetic treatment. For example, the gel or liquid composition may be comprised of a hyaluronic acid gel filler, collagen, calcium hydroxylapatite, poly-L-lactic acid or related gel or liquid compositions.

In accordance with the first preferred embodiment of the method for percutaneous administration of a liquid or gel composition of the invention, an injection device is used, preferably the conical needle 210 attached to a syringe.

The first preferred embodiment of the conical needle 210 described herein may be manufactured by any suitable method. These methods of manufacturing may include but are not limited to molding and die casting. The conical needle 210 may also be manufactured by bending a blunt needle at the longitudinal axis and turning or grinding to produce the sharp point and conical shape of the conical portion 250.

Referring to FIGS. 1A-1C the prior art standard beveled needle 110 includes a needle body 120 including the beveled face 140 at the distal end and a proximal end adapted for attachment to a syringe. The beveled face 140 is configured for penetration into the body cavity of a subject, and a fluid pathway 180 extends completely through the needle body 120 concentrically along the longitudinal axis. The needle body 120 of prior art beveled needle 110 includes an exterior surface 130 with a beveled face 140 at the distal end of needle body 120. An opening 150 that is concentrically positioned on the longitudinal axis is formed in the beveled face 140 and is in fluid communication with the fluid pathway 180. The beveled face 140 includes a sharp cutting edge 160 for penetrating the tissue of the subject. Referring to FIG. 1B, a front view of the distal end of prior art beveled needle 110 is illustrated with the beveled edge 140, the opening 150 and the sharp cutting edge 160. Referring to FIG. 1C, a cross-sectional view of prior art beveled needle 110 is illustrated with the needle body 120, the exterior surface 130 with the sharp cutting edge 160 at the distal end. Additionally, the needle body 120 includes an interior surface 170 that defines the fluid pathway 180 extending completely through needle body 120.

Figure 2:
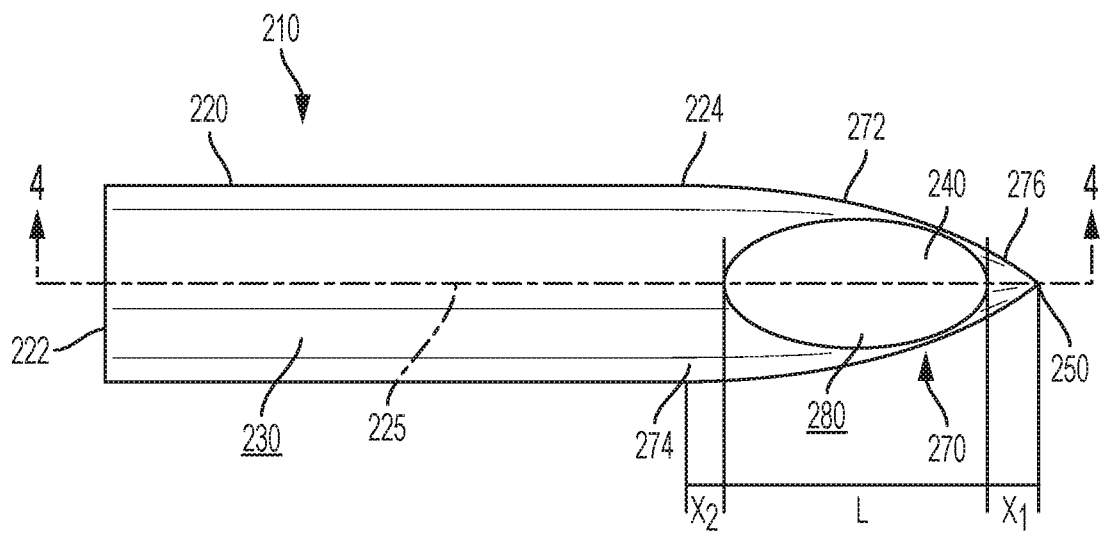
FIG. 2 is a top plan view of a first preferred embodiment of a conical needle of the present invention.

Referring to FIG. 2, a top plan view of conical needle 210 in accordance with the first preferred embodiment of the present invention is illustrated, which includes the needle body 220 with the proximal end 222, the distal end 224, and an exterior surface 230. The conical needle 210 further has a conical portion 270 with a sidewall 272, a distal end 276, and a proximal end 274, with a sharp tip 250 at the distal end 276 of the conical portion 270. The sidewall 272 is preferably cone-shaped and smooth around the entire perimeter of the needle 210 such that there are no ridges or sharp surfaces located anywhere along the sidewall 272. Such smoothness and lack of ridges or sharp surfaces further enables the reduction in bruising of a patient by reducing the possibility of damaging any subcutaneous blood vessels, as the smooth conical shape is more likely to simply displace any such blood vessels rather than piercing them.

Figure 4:
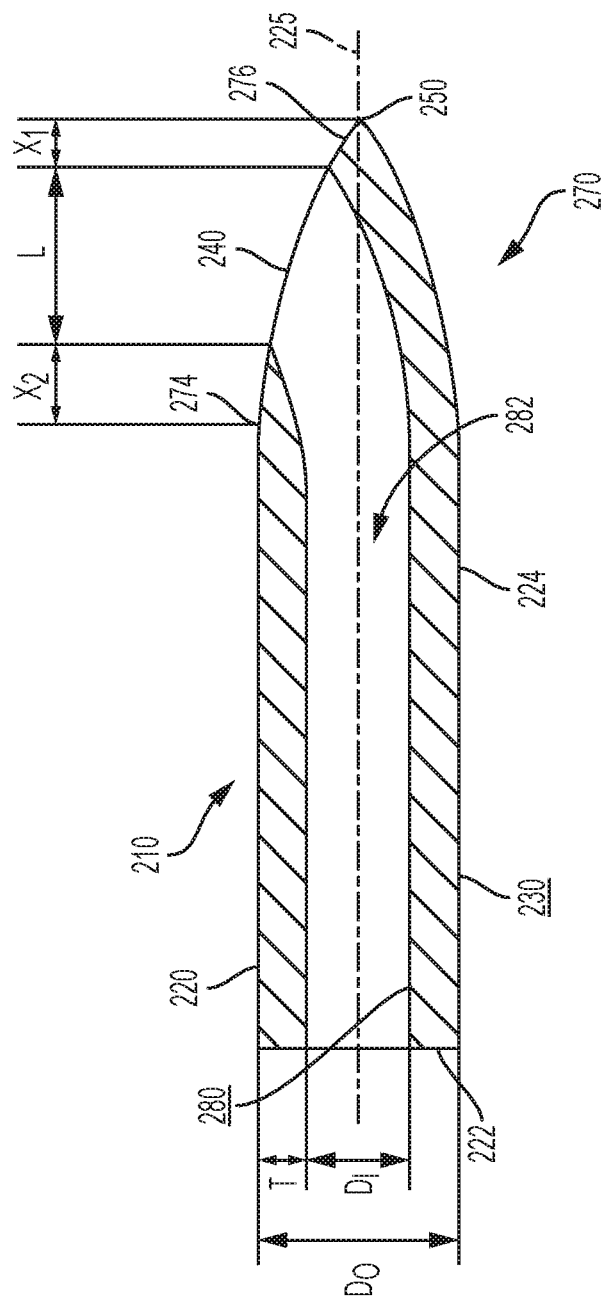
FIG. 4 is a cross-sectional view of the conical needle of FIG. 2, taken along line 4-4 of FIG. 2.

The lateral or injection opening 240 is formed in the conical portion 270 such that the entire opening 240 is positioned in the conical portion 270 or extends through the sidewall 272 of the conical portion 270. The lateral or injection opening 240 is, therefore, positioned entirely between the sharp tip 250 and the transition between the proximal end 274 of the conical portion 270 and the distal end 224 of the substantially cylindrical needle body 220. The lateral opening 240 is also preferably located nearer to the sharp tip 250, as defined by a tip distance $X_1$, than to the transition between the proximal end 274 of the conical portion 270 and the distal end 224, as defined by a body distance $X_2$. More preferably, the tip distance $X_1$ is smaller than the opening width W and smaller than the opening length L. Most preferably, the tip distance $X_1$ is less than approximately eighteen hundredths millimeters (0.18 mm) or is approximately equal to a wall thickness T of the needle body 220 or approximately seventy-six thousandths millimeters (0.076 mm) to ten hundredths millimeters (0.10 mm) for the preferred twenty-seven to twenty-nine gauge (27-29 G) first preferred conical needle 210. In the first preferred embodiment, the body distance $X_2$ is approximately equal to the wall thickness W and the tip distance $X_1$ or, preferably, approximately eighteen hundredths millimeters (0.18 mm) or approximately seventy-six thousandths millimeters (0.076 mm) to ten hundredths millimeters (0.10 mm) for the preferred twenty-seven to twenty-nine gauge (27-29 G) first preferred conical needle 210. The tip distance $X_1$, body distance $X_2$ and wall thickness T are not limited to being substantially equal or to being in the above-defined range and may have different dimensions that fall outside of the preferred range, particularly when different gauge conical needles 210 are employed, such as seven to thirty-fourth gauge (7-34 G) conical needles 210, which preferably have tip distances $X_1$, body distances $X_2$ and wall thicknesses T in the range of approximately fifty-one thousands millimeters to thirty-eight hundredths millimeters (0.051-0.38 mm). The lateral opening 240 is in fluid communication with the fluid pathway 282, as shown in FIG. 4. The fluid pathway 282 extends through the needle body 220 from the lateral opening 240 to the proximal end 222 of the needle body 220. The lateral opening 240 is preferably ovular in shape, but may also be any other shape suitable for delivering fluids to a patient.

Figure 3:
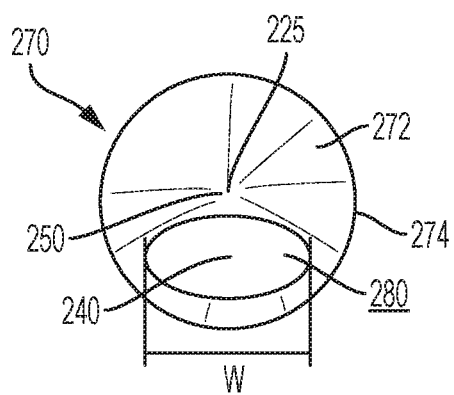
FIG. 3 is a front elevational view of the conical needle of FIG. 2.

Referring to FIG. 3, a front view of the distal end 276 of the conical portion 270 of the conical needle 210 of the first preferred embodiment is illustrated with the sidewall 272, the proximal end 274, the distal end 276, the lateral opening 240 positioned between the proximal and distal ends 274, 276, and the sharp tip 250. In the first preferred embodiment, the opening width W is approximately twice the wall thickness T, but is not so limited and may be otherwise constructed depending on user and/or designer preferences or requirements. The first preferred conical needle 210 has an opening width W in the range of approximately thirty hundredths millimeters to forty hundredths millimeters (0.30-0.40 mm) and a wall thickness of approximately fifteen hundredth millimeters to twenty hundredths millimeters (0.15-0.20 mm) for the preferred twenty-seven to twenty-nine gauge (27-29 G) conical needles 210.

Referring to FIG. 4, a cross-sectional view of the conical needle 210 is illustrated with the needle body 220 and the exterior surface 230 with the sharp tip 250 at the distal end 276 of the conical portion 270. The needle body 220 includes an interior surface 280 that defines the fluid pathway 282 that extends from the proximal end 222 of needle body 220 toward the sharp tip 250 at the distal end 276 of conical portion 270. The lateral injection opening 240 is positioned completely in the conical portion 270 between the proximal and distal ends 274, 276 of the conical portion 270. As shown in FIG. 4, the cross-sectional shape of the conical portion 270 may be arcuate, such that the sidewall 272 has an arcuate shape from its proximal end 274 to its distal end 276, but is not so limited. The conical portion 270 may also take any other suitable shape or profile, such as being linear from the proximal end 274 to the distal end 276 to substantially form a cone.

Figure 5A:
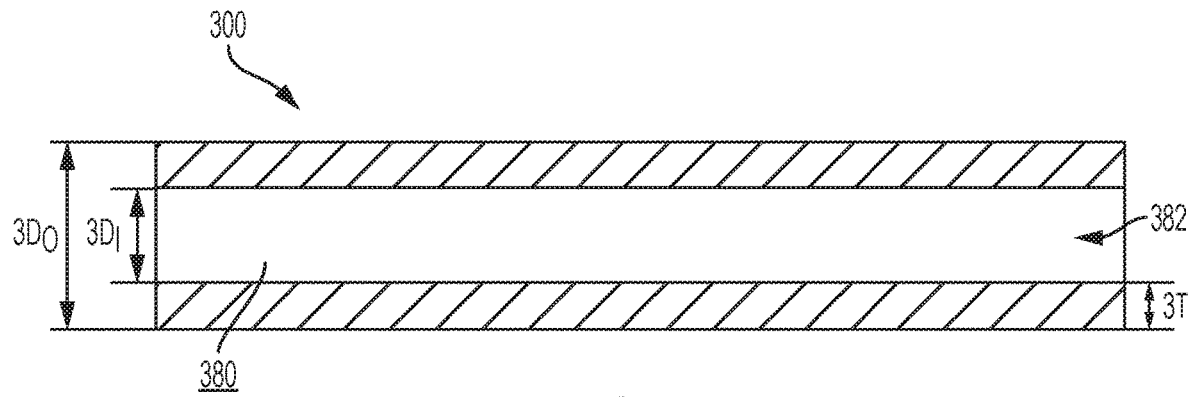
FIG. 5A is a cross-sectional view a second preferred embodiment of a conical needle after a first manufacturing step.
Figure 5B:
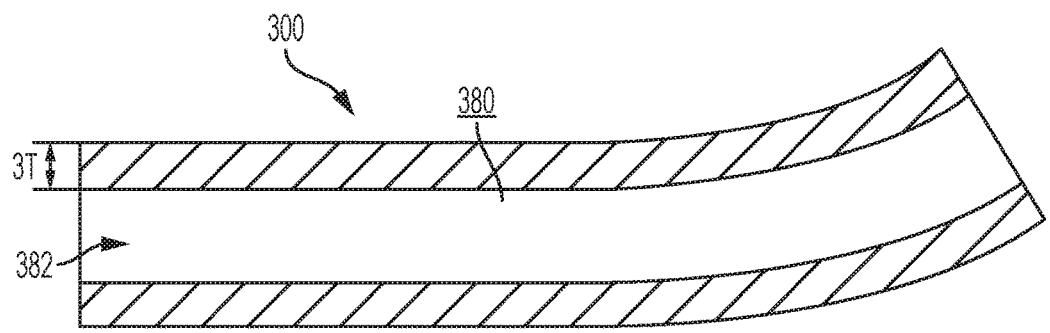
FIG. 5B is a cross-sectional view of the conical needle of FIG. 5A after a second manufacturing step.
Figure 5C:
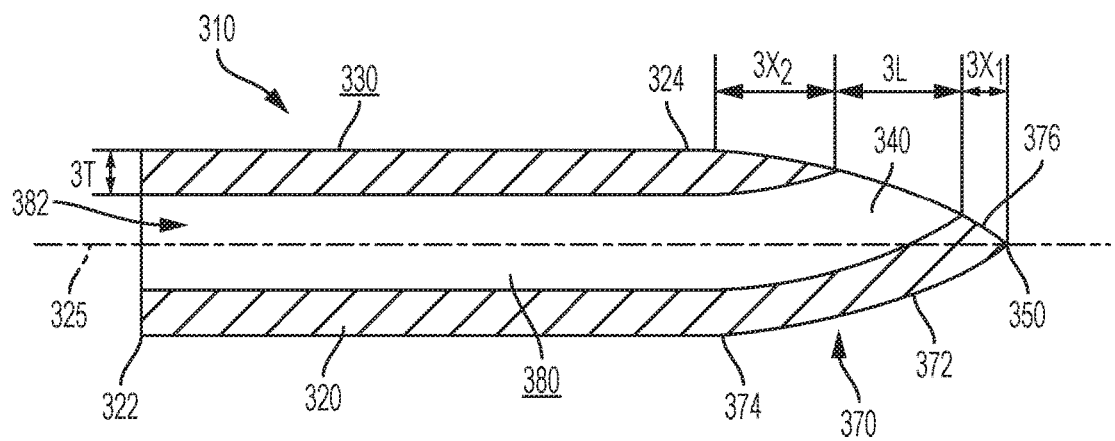
FIG. 5C is a cross-sectional view of the conical needle of FIG. 5A after a third manufacturing step.

Referring again to FIGS. 1A-1C, prior art beveled hypodermic needles are typically manufactured by drawing steel or stainless steel through dies to create a hollow shaft. The hollow shaft is then cut at an angle to create the sharp, beveled shape as shown in FIGS. 1A-1C. As shown in FIGS. 5A-5C, a second preferred embodiment of the conical needle 310 is manufactured by first drawing steel or other material through a die to create the blunt, hollow needle 300 shown in FIG. 5A. The second preferred embodiment of the conical needle 310 has a similar construction to the first preferred conical needle 210 and like reference numbers are utilized to identify like features of the second preferred conical needle 310 with a number "3" prefix replacing the "2" prefix to distinguish the features of the conical needle 210 of the first preferred embodiment from the conical needle 310 of the second preferred embodiment. The blunt, hollow needle 300 is then turned or bent to a desired angle to create the bent needle 305 shown in FIG. 5B. Finally, the bent needle 305 is ground to form the conical needle 310 shown in FIG. 5C. Such a process results in the second preferred conical needle 310 having a conical portion 370, the conical portion 370 having the sharp tip 350 at the distal end 376 of the conical portion 370 and the lateral opening 340 located fully within the sidewall 372 of the conical portion 370.

The angle to which the blunt, hollow needle 300 is bent to form the bent needle 305 shown in FIG. 5B, the angle at which the bent needle 305 is ground to form the conical needle 310 shown in FIG. 5C, the outer wall diameter $3D_O$, and the inner wall diameter $3D_I$, and the wall thickness 3T, may all affect the dimensions of the lateral opening 340. As shown in FIG. 5C, the second preferred embodiment has the tip distance $3X_1$ approximately equal to the wall thickness 3T, the opening length 3L is approximately twice to three times that of the tip distance $3X_1$, wherein the body distance $3X_2$ is approximately the same as or slightly smaller than the opening length 3L. In the second preferred embodiment, the opening width (not shown) is approximately equal to the inner wall diameter $3D_I$, while the opening length 3L is also approximately fifth percent (50%) larger than the inner wall diameter $3D_I$.

The second preferred conical needle 310 is also preferably sized as a twenty-seven to twenty-nine gauge needle, wherein the outer wall diameter $3D_O$ is approximately forty-one to thirty-three hundredths millimeters (0.41-0.33 millimeters), the inner wall diameter $3D_I$ is approximately twenty-one to eighteen hundredths millimeters (0.21-0.18 mm) and the wall thickness 3T is approximately ten hundredths to seventy-six thousandths millimeters (0.10-0.076 mm), but is not so limited. The second preferred conical needle 310 may be constructed of nearly any sized needle that is able to take on the general size and shape of the second preferred conical needle 310, withstand its normal operation conditions and perform the preferred functions of the second preferred conical needle 310, as is described herein. The conical needle, for example, may be constructed of a needle having a needle gauge from seven to thirty-four (7-34 G). The second preferred conical needle, therefore, may have an outer wall diameter $3D_O$ between approximately four and six tenths millimeters and eighteen hundredth millimeters (4.6-0.18 mm), an inner wall diameter $3D_I$ between approximately three and eight tenths millimeters and eighty-three thousandths millimeters (3.8-0.083 mm) and a wall thickness between approximately thirty-eight hundredths and fifty thousandths millimeters (0.38-0.050 mm).

The second preferred conical needle 310 constructed in the preferred twenty-seven to twenty-nine gauge (27-29 G) sizes has the wall thickness 3T and the tip distance $3X_1$ in the range of approximately ten hundredths to seventy-six thousandths millimeters (0.10-0.076 mm) and the opening width 3W and the inner wall diameter $3D_I$ being in the range of approximately twenty-one hundredths to eighteen hundredths millimeters (0.21-0.18 mm). Utilizing the preferred twenty-seven to twenty-nine gauge (27-29 G) sizes, the opening length 3L and body distance $3X_2$ are approximately double to two and two-thirds (2-2⅔×) greater than the wall thickness 3T or in the range between approximately twenty-seven hundredths to fifteen hundredths millimeters (0.27-0.15 mm).

Referring to FIGS. 2, 4 and 5C, the first and second preferred conical needles 210, 310 include the lateral opening 240, 340 located fully or entirely within the sidewall 272, 372 or extending through the sidewall 272, 372 of the conical portion 270, 370. The sharp tip 250, 350 is positioned on the longitudinal axis 225, 325 and the sidewall 272, 372 is substantially solid or continuous between the sharp tip 250, 350 and the front end of the lateral opening 240, 340. The conical needle 210, 320 is, therefore, able to penetrate the patient's skin with the sharp tip 250, 350 and urge vessels out of the way during penetration with the solid sidewall 272, 372, before the skin encounters any discontinuity, such as the lateral opening 240, 340. The conical needle 210, 310, in this way, reduces damage to vessels near the penetration site. In addition, the lateral opening 240, 340 is relatively close to the sharp tip 250, 350 such that the liquid or gel may be injected near the sharp tip 250, 350, which limits the depth or penetration required for the conical needle 210, 310 to inject the liquid or gel. These features provide for a relatively shallow depth of injection and a relatively atraumatic injection that is particularly suited for cosmetic injections where bruising and trauma at and near the injection site are particularly undesirable. The relatively shallow injection depth is facilitated by positioning the opening 240, 340 entirely in the conical portion 270, 370 with the tip distance $X_1$, $3X_1$ being substantially equal to the wall thickness T, 3T and being smaller than the opening length L, 3L and the opening width W. This combination of features minimizes bruises when conducting medical injections, particularly injections for cosmetic purposes with cosmetic or medical liquids or gels.

It will be appreciated by those skilled in the art that changes could be made to the embodiments described herein without departing from the broad inventive concept thereof. It is understood, therefore, that this invention is not limited to the particular embodiments disclosed, but it is intended to cover modifications within the spirit and scope of the present invention as defined by the appended claims.

I claim:

1. A conical needle comprising:
   a hollow needle body having a distal end and a proximal end, the hollow needle body having a substantially consistent cross-sectional diameter along the entire length of a longitudinal axis of the hollow needle body between the proximal end and the distal end of the hollow needle body, the interior of the hollow needle body defining a fluid pathway extending along the longitudinal axis;
   a conical portion located at the distal end of the hollow needle body, the conical portion defining a single, smooth sidewall, a distal end, a proximal end, and a transition portion between the distal end and the proximal end, the conical portion forming a conical tip located at the distal end of the conical portion, the conical tip having a sharp point positioned on the longitudinal axis, the conical portion integrally formed with the hollow needle body; and
   an ovular lateral opening located fully within the sidewall of the conical portion, the ovular lateral opening being in fluid communication with the fluid pathway, the conical portion and the ovular lateral opening define a tip distance and an opening length, the opening length being greater than the tip distance,
   wherein the ovular lateral opening and the conical portion also define a body distance between the ovular lateral opening and the proximal end of the transition portion, and
   wherein the body distance being substantially equal to the opening length.

2. The conical needle of claim 1, wherein the proximal end of the hollow needle body is configured to mount to a syringe.

3. The conical needle of claim 1, wherein the sidewall of the conical portion has an arcuate shape.

4. The conical needle of claim 1, wherein the conical needle is constructed of a polished surgical steel.

5. The conical needle of claim 1, wherein the fluid pathway is positioned coaxially on the longitudinal axis in the hollow needle body and extends away from the longitudinal axis in the conical portion.

6. The conical needle of claim 1, wherein the ovular lateral opening has an opening width, the opening length greater than the opening width.

7. The conical needle of claim 1, wherein the hollow needle body defines a wall thickness, the tip distance being substantially equal to the wall thickness.

8. The conical needle of claim 1, wherein the opening length is at least double the tip distance.

9. The conical needle of claim 1, wherein the ovular lateral opening and the conical portion define a body distance and an opening width, the tip distance being smaller than the opening width.

10. The conical needle of claim 1, wherein the conical portion and the ovular lateral opening define a body distance, the tip distance being substantially equal to the body distance, the opening length being greater than the body distance.

11. The conical needle of claim 1, wherein the conical portion and the ovular lateral opening define a body distance, the tip distance being less than the body distance, the opening length being greater than the body distance.

12. The conical needle of claim 1, wherein the conical portion and the lateral opening define a body distance, the tip distance being less than the body distance, the opening length being substantially equal to the body distance.

13. The conical needle of claim 1, wherein the ovular lateral opening is smooth relative to all adjacent exterior surfaces of the conical portion such that the ovular lateral opening forms no cutting edges and avoids tissue damage.

14. The conical needle of claim 2, wherein the proximal end of the hollow needle body is further configured to place the fluid pathway into fluid communication with the syringe.

15. The conical needle of claim 6, wherein the opening length is within the range of thirty-three hundredths to forty-two hundredths millimeters (0.33-0.42 mm) and the opening width is within the range of eighteen to twenty-one hundredths millimeters (0.18-0.21 mm).

16. The conical needle of claim 9, wherein the hollow needle body has an outer wall diameter and an inner wall diameter, the inner wall diameter being substantially the same as the opening width.

17. The conical needle of claim 6, wherein the opening length is at least double the opening width.

18. A method for manufacturing a conical needle, the method comprising the following steps:
   bending or turning a blunt-tipped, hollow needle having a longitudinal axis; and
   grinding a tip portion of the blunt-tipped, hollow needle to form a conical portion having a proximal end, a distal end, a transition portion between the distal end and the proximal end, and a sharp tip at a distal end of the conical portion, the sharp tip positioned on the longitudinal axis, and a lateral opening located fully within a sidewall of the conical portion,
   wherein the lateral opening and the conical portion also define a body distance between the lateral opening and the proximal end of the transition portion, the body distance being substantially equal to the length of the lateral opening.

19. A conical needle comprising:
a hollow needle body having a distal end and a proximal end, the hollow needle body having a substantially consistent cross-sectional diameter along the entire length of a longitudinal axis of the hollow needle body between the proximal end and the distal end of the hollow needle body, the interior of the hollow needle body defining a fluid pathway extending along the longitudinal axis;
a conical portion located at the distal end of the hollow needle body, the conical portion defining a single, smooth sidewall, a distal end, a proximal end, and a transition portion between the distal end and the proximal end, the conical portion forming a sharp tip located at the distal end of the conical portion, the conical portion integrally formed with the hollow needle body; and
an ovular lateral opening located fully within the sidewall of the conical portion, the ovular lateral opening being smooth relative to all adjacent exterior surfaces of the conical portion such that the ovular lateral opening forms no cutting edges and avoids tissue damage, the ovular lateral opening being in fluid communication with the fluid pathway, the conical portion and the ovular lateral opening define a tip distance and an opening length, the opening length being greater than the tip distance,
wherein the ovular lateral opening and the conical portion also define a body distance between the ovular lateral opening and the proximal end of the transition portion, and
wherein the body distance being substantially equal to the opening length.

* * * * *